United States Patent [19]

Nolan

[11] Patent Number: 5,093,253

[45] Date of Patent: Mar. 3, 1992

[54] METHOD FOR MICROBIAL IMMOBILIZATION BY ENTRAPMENT IN GELLAN GUM

[75] Inventor: Carol L. Nolan, Blue Bell, Pa.

[73] Assignee: Monsanto Company, St. Louis, Mo.

[21] Appl. No.: 547,565

[22] Filed: Jul. 2, 1990

Related U.S. Application Data

[63] Continuation-in-part of Ser. No. 433,069, Nov. 6, 1989, abandoned, which is a continuation of Ser. No. 34,200, Apr. 6, 1987, abandoned.

[51] Int. Cl.$^5$ .................. C12N 11/10; C12N 11/04; C12N 1/20; C12P 1/04
[52] U.S. Cl. .................. 435/178; 435/170; 435/182; 435/252.33; 435/849
[58] Field of Search .............. 435/170, 174, 177, 178, 435/179, 182, 252.33, 849; 424/93

[56] References Cited

U.S. PATENT DOCUMENTS

| | | | |
|---|---|---|---|
| 4,352,883 | 10/1982 | Lim | 435/178 |
| 4,452,892 | 6/1984 | Rosereer | 435/178 X |
| 4,526,867 | 7/1985 | Chibata et al. | 435/178 |
| 4,701,326 | 10/1987 | Nelson et al. | 424/93 |

Primary Examiner—David M. Naff
Attorney, Agent, or Firm—Paul L. Passley; James W. Williams, Jr.

[57] ABSTRACT

Microbial cells are immobilized by entrapment in gellan gum, also known as deacetylated heteropolysaccharide S-60. Entrapment can be carried out by forming a mixture of a paste of microbial cells and an aqueous solution of gellan gum and adding the mixture drop-wise to an aqueous solution of cations to produce beads of hardened gellan gum entrapping the microbial cells. The microbial cells preferably contain aspartase activity and can be *E. coli* ATCC 11303, and the cations are preferably magnesium ions. In an alternative embodiment, the mixture of microbial cell paste and aqueous gellan gum solution is admixed with a porous cationic exchange resin which is preferably in magnesium ion form and the microbial cells are entrapped in hardened gellan gum in and on the resin.

14 Claims, No Drawings

METHOD FOR MICROBIAL IMMOBILIZATION BY ENTRAPMENT IN GELLAN GUM

RELATED APPLICATIONS

This application is a continuation-in-part of application Serial No. 07/433,069 filed November 6, 1989.

BACKGROUND OF THE INVENTION

The present invention relates to immobilized microbial cells which are catalytically-active and to a method for preparing same in which the immobilization is effected by means of entrapping whole microbial cells or catalytically active biological material with a composition essentially comprising a polysaccharide containing glucuronic acid, rhamnose and glucose. Various techniques have been proposed for immobilizing microbial cells and enzymes on water-insoluble supports. These methods have included covalent chemical linkage to a support using functional groups of the enzyme that are not essential for enzymatic activity; entrapment of the microbial cell or enzyme within a hydrophilic gel lattice which retains the catalytically-active material while permitting substrate and product to pass through; ionic binding or physical absorption on hydrophilic ion exchange resins or on charcoal or glass beads and aggregating the enzymes by cross-linking with bifunctional compounds.

Entrapment methods of immobilization are most versatile. For example, U.S. Pat. No. 3,791,926 discloses methods of entrapping microbial cells and enzymes within polymer matrices U.S. Pat. No. 3,957,580 discloses a method of entrapping microbial cells within polymer systems in which the immobilized cells are further cross-linked to the polymer matrix using polyfunctional reagents such as glutaraldehyde.

However, synthetic polymer systems of the types described above have several drawbacks. The preparation of immobilized cells may involve the use of toxic materials such as monomers, initiators and cross-linkers linkers. The support matrix can deform or compress upon use in a commercial-scale bioreactor system.

Accordingly, it is the overall object of the present invention to provide a method of immobilizing, catalytically-active microbial cells which maintains enzymatic activity.

It is another object of the present invention to provide a method of immobilizing catalytically-active microbial cells which results in compositions exhibiting good mechanical strength.

It is still another object of the present invention to provide an immobilization method which results in compositions exhibiting kinetics comparable to soluble enzymes.

It is yet another object of the present invention to provide an immobilization method which uses an encapsulation polymer which is easy to use and inexpensive.

These and other objects and advantages will be evident from the following description and illustrative examples.

DESCRIPTION OF THE INVENTION

The present invention provides an improved method for microbial cell immobilization in which the cells are encapsulated in a composition essentially comprising a polysaccharide containing glucuronic acid, rhamnose and glucose. More particularly, the invention employs the use of a composition known as gellan gum. For purposes of the present invention, by "gellan gum" is meant the deacetylated heteropolysaccharide S-60 as described and claimed in U.S. Pat. No. 4,326,052 issued April 20, 1982 to K. S. Kang et al. The immobilized cell preparations which result from the present method show surprising advantages over previously disclosed encapsulation methods: mechanical strength, enzymatic stability, easy/inexpensive preparation and kinetics comparable to the soluble enzyme.

The preferred method of obtaining stable, immobilized, catalytically-active substances is by hardening droplets formed from a mixture of microorganisms, gellan gum and water with a solution of $MgSO_4$ or other salt containing monovalent or divalent cations. Although various other shapes are possible, spherical beads are preferred since this shape affords the greatest surface area per unit volume. The present method allows significant flexibility in determining the mechanical strength of the encapsulated material. In the present method, 1.0 to 1.8 wt.%, preferably 1.2 to 1.8 wt.%, gellan gum is dissolved in deionized water, heated to at least 80° C. and cooled to about 25-55° C., and mixed with a paste of microorganisms weighing not more than 50% of the weight of the gellan gum solution, preferably less than about 25%. The gellan gum/cell mixture is shaped in the form of beads by conventional methods known in the art and then is preferably contacted with about 0.1-0.5 M, preferably about 0.1-0.4 M, solution of magnesium sulfate ($MgSO_4$) or another divalent cationic salt at room temperature. The resulting beads are allowed to harden for about 10 minutes and are then filtered from the $MgSO_4$ solution. If desired, the magnesium sulfate solution may be reused. If monovalent cationic salt solutions are used to harden the beads, higher concentrations, about 0.5-2.0 M salt, are required. The preferred limits on the allowable concentrations of gellan gum, cell paste and $MgSO_4$ solution are narrow since conditions outside of these ranges yield beads that are either too compressible or a mixture that is too viscous to be easily shaped into beads and prone to premature hardening.

Beads may be easily formed by forcing the gellan gum/cell mixture through a small bore pipette or syringe. The size of the bead may be controlled by a concentric flow of air around the pipette or syringe. Other methods of bead making may be employed such as those described by C. D. Scott, 1985 Int'l Enzyme Conference; U. Matulovic et al., *Biotechnology Letters*, Vol. 8, No. 7, pp 485-490 (1986); T. Rehg et al., *Biotechnology Letters*, Vol. 8, No. 2, pp 111-114 (1986); and A. C. Hulst et al., *Biotech Bioenqr.*, Vol. 17, pp 870-876 (1985).

It has been found that unlike other entrapment methods, the use of gellan gum is very sensitive to the conditions selected. One reason for this sensitivity is the small amount of gellan gum used in the present method. About one-half to one-third as much gellan gum is used in comparison to carrageenan and the resulting beads are mechanically stronger.

Small variations in the concentration of gellan gum provide flexibility in the type of bead which is formed. The gellan gum concentration should be sufficient to produce beads with adequate strength for the anticipated use but low enough to prevent premature hardening of the gellan gum. Initial concentrations (before the addition of cell paste) of gellan gum should not be below about 1.0%, preferably about 1.2% and more preferably 1.2-1.6%, or the beads will be easily deformed and, in many cases, unsuitable for column reactors. Initial concentrations of gellan gum above 1.8 wt.% may create problems in dispensing the gellan gum/cell mixture into droplets without premature hardening of the mixture in transfer lines due to cations present in the gellan gum solution.

It has been found that even with the broad use range of 1.0–1.8% or the preferred use range of 1.2–1.8% residual material present in the cell paste can cause the gellan gum to set up when the cells are added depending upon the fermentation medium used to grow the cells. Therefore, to improve control of the immobilization procedure, the cells are preferably washed in deionized water to remove residual salts from the medium, before the cells are combined with the gellan gum. The cell wash step affords better control of the solidification process. That is, the substantially cation-free cell paste can be added to the gellan gum at a lower temperature without premature solidification. Cells can also be washed in other non-ionic solutions of sufficient osmotic strength to prevent cell lysis. Suitable non-ionic solutions include sugar solutions, such as dextrose and sucrose. The cell wash step can be eliminated, but then the amount of cell paste used for a given amount of gellan gum must be reduced. By washing the cells, one may often be able to increase the cell density, and hence density of activity in the immobilized preparation, with a corresponding increase in volumetric productivity of the bioreactor.

Similarly, the procedure is also sensitive to the wetness of the cell paste. Too much water present with the cells will dilute the final concentration of gellan gum below the critical levels needed for acceptable bead formation. The cell paste should be as concentrated as possible, diluted only enough to enable easy transfer and mixing. For purposes of the present invention, the cell content of the cell paste is about 14 wt.% based on the dry weight of the cells contained therein. The cell paste should preferably account for less than about 50% of the weight of the gellan gum/cell paste mixture or else the beads will be too soft. A cell paste content of less than 25 wt.% is preferred in many cases. If the cell content of the paste is greater than 14%, the cell paste may account for more than 50% of the mixture. The concentration of Mg ion is not as critical, but at concentrations below 0.1 M there is a noticeable reduction in bead strength.

The immobilized catalytically-active substance prepared according to the above procedure has surprising stability without the additional cross-linking treatments which are normally required for other encapsulation methods. Indeed, in one embodiment it has been determined that the half-life for aspartase activity in $E.$ $coli$ cells ATCC 11303, encapsulated according to the above procedure, is at least 150 days. This degree of stability is unexpected in light of the fact that the same cells encapsulated in carrageenan without glutaraldehyde treatment only show a 70–90 day half-life, see U.S. Patent 4,526,867. Since the half-life of the free cells is only about 17 days, the immobilization with gellan gum significantly extends the useful time period in which the cells can be utilized for enzymatic reactions.

Activity losses upon immobilization are negligible because of the mild conditions required for encapsulation and hardening. Glutaraldehyde treatment, which may destroy some activity while imparting stability, is not required but may be used without adversely affecting immobilization. Freshly harvested $E.$ $coli$ cells ATCC 11303 show 7–8 fold lower aspartase activity than the same cells immobilized and activated for 24 hours in substrate at 37° C. The free cells require about 3 days in substrate to reach their peak activity, while immobilized cells are at maximum after 18–24 hours. These differences in timing for peak activity make it difficult to compare activity levels in free cells vs. immobilized cells. Published information on activity retention for other encapsulation methods does not give specifics for timing of assays. The critical timing of activity determinations is shown by the fact that immobilization of free cells at their peak (3 days) activity does not produce an immobilized preparation with as much activity as if fresh cells (with lower activity) were encapsulated.

Those skilled in the art recognize that enzymes which are encapsulated into polymeric substances often have increased Michaelis constants because of the difficulty of diffusing even low molecular weight substrates into the matrix. The $K_m$ for soluble aspartase is reported to be 0.15 M (Sato et al., BBA. 570, 179–186 1979). The $K_m$ for gellan gum immobilized $E.$ $coli$ cells ATCC 11303 containing aspartase was measured experimentally to be 0.2–0.25 M. The fact that the $K_m$ for the gellan gum system is close to that of the soluble enzyme is indicative of an immobilization method that does not add hindering environmental effects to the enzyme. This result is entirely unexpected because the $K_m$ for aspartase in carrageenan entrapped $E.$ $coli$ cells is 0.71–0.85 M (Sato, 1979). Low apparent Michaelis constant is a desirable and surprising advantage to gellan gum immobilization.

In another embodiment of the present invention, gellan gum can be coated onto ion exchange resin beads and hardened by the cations on the resin. The advantages of this embodiment are: small, mechanically stable beads with thinner transport layers. This is a novel method of cross-linking a gelling agent. Indeed, all prior art methods require a soluble cation to harden the matrix. In this type of embodiment, it is preferred that the gellan gum harden within the pores of the resin as well as on the outer surface. This requires that the pores of the resin be large enough to accommodate the microbial cells to be immobilized. If the pores are too small the gellan gum/cell mixture will be forced to the exterior surface of the bead which would, in many cases, not have sufficient cation density to harden the gel.

This invention is equally applicable for a variety of enzyme systems. For example, penicillin acylase, glucose isomerase, glucose oxidase, fumarase, phenylalanine ammonia lyase, aspartate amino transferase, invertase, cis-trans maleic isomerase, sorbitol dehydrogenase, L-aspartate beta-decarboxylase and others can all be prepared by the process of this invention. When penicillin acylase is desired, cells of Proteus rettgeri can be employed. When immobilization of cells containing glucose isomerase, glucose oxidase, fumarase, invertase, cis-trans maleic isomerase, sorbitol dehydrogenase, L-aspartate beta-decarboxylase or others is desired, microorganisms which may be used can include those of the genera Streptomyces, Bacillus, Acetobacter, Pseudomonas and Aspergillus. Microorganisms of this type may not necessarily be intact living cells, but may be physically or chemically treated prior to use in the present invention.

Those skilled in the art recognize that the present system will be suitable for entrapping partially purified or purified enzymes. Indeed, this approach may be useful in cases where the enzyme of interest is susceptible to attack by proteases. Alternately, in some cases one may desire to remove other enzymes present in the microbial cell which would further catabolize the desired reaction product. In cases where the purified enzymes may leach from the gellan gum bead, one may reduce the loss of enzyme by including a small amount of gelatin and cross-linking with a suitable chemical agent such as glutaraldehyde.

EXAMPLES

The following examples are provided to better elucidate the practice of the present invention and are, in no way, intended to limit the scope of the present invention.

EXAMPLE 1

E. coli cells ATCC 11303 were grown under standard fermentation conditions in shake flasks. The broth was centrifuged at 8000 ×gravity for 8 minutes to give a cell paste. About 1.2 grams of cell paste were obtained from 100 ml of broth. The cells were washed in deionized (Milli-Q) water by resuspending 4 gms. of cells in 5 ml. water, centrifuging 5 min. at 8000 ×gravity, followed by a second wash step. A gellan gum solution was prepared by adding 0.24 gm. gellan gum to 19.6 ml. water, heating the mixture to 90° C. with stirring and then cooling the mixture to 54° C. The washed cells were slurried in 1 ml. water and then added to the 54° C. gellan gum solution. The gellan gum/cell mixture was immediately pipetted dropwise into a 0.2 M $MgSO_4$ solution maintained at room temperature. The beads were gently agitated for 10 minutes to complete hardening and then were vacuum filtered from the $MgSO_4$ solution. The final weight of the immobilized preparation was 16.9 grams. The immobilized cells were incubated overnight at 37° C. in 1.5 M fumaric acid substrate solution. The immobilized cells later showed a rate of 0.0253 moles aspartic produced per gm. cells-hours.

EXAMPLE 2

A highly porous (pore diameter 1 micron) cationic exchange resin is put into $Mg^{++}$ ion form using standard techniques. The resin is then dried. A 1 wt.% solution of gellan gum in deionized water is made by dissolving 0.08 gm. of gellan gum in 8 ml. of deionized water. The gellan gum solution is heated to about 80° C. and then cooled to about 40° C. E. coli cells ATCC 11303, obtained as described in Example 1, are added to the above-described gellan gum in the amount of about 1 gm. of cell paste per 8 ml. of gellan gum solution. The gellan gum/cell mixture is coated onto the dry porous cationic exchange resin by hard-stirring the resin with the gellan gum/cell mixture at about 40° C and then permitting the material to cool to room temperature (~25° C.). A sufficient amount of resin is used so that essentially all the material is taken up by the resin. Upon cooling, the gellan gum will harden entrapping the cell in and on the resin beads.

EXAMPLE 3

Immobilized E. coli cells ATCC 11303 were prepared as described in Example I. A column bioreactor was loaded with immobilized cells for half-life determination. The feed stream to the column was 1.5 M $NH_4$-fumarate (technical grade), 1 mM $MgSO_4$, at pH 8.5.

During days 1–19 the column was operated 8 hours/day at variable feed rates and included a three-day period when malfunctioning temperature control resulted in approximately 20% loss of enzyme. The bioreactor was then operated 24 hours/day at variable feed rates from day 20 to day 30. Stability data was also obtained from day 31 to day 66 at a feed rate of two bed-volumes per hour and at 37° C.

The kinetic data indicates a zero time intercept of 67% conversion at two bed-volumes per hour feed rate. Linear regression analysis of the stability data projects a half-life of about 150 days.

For comparison, the half-life of free cells grown in glycerol-fumarate medium, calculated as the time for activity to reach 50% of the peak level, is estimated to be about 17 days. The above data was obtained using batch reactions of 2 hours at 37° C and 1.5 M $NH_4$-fumarate at pH 8.5.

EXAMPLE 4

This Example shows that hydrogels of carrageenan, agar and alginic acid are not suitable for making acceptable quality beads of immobilized aspartase in accordance with this invention for one or more reasons.

Hydrogels of carrageenan, agar and alginic acid having acceptable pH's were prepared by mixing powders of the materials with water, heating to dissolve the powders to form solutions and cooling the solution to make the gels. However, in the case of alginic acid cooling was not sufficient to obtain the gel and the gel was formed by replacing the $MgSO_4$ with $CaCl_2$ in the preparation of the gel.

It is known that if calcium is present with immobilized microorganisms that calcium fumarate is formed during the conversion of ammonia fumarate to ammonia aspartate by aspartase. Calcium fumarate is a contaminant for aspartate and is, therefore, avoided by this invention. Alginic acid hydrogels are known to be hardened by adding calcium to the hydrogel or dropping beads of alginic acid hydrogels into a calcium solution. Applicant has found that hydrogels of the gellan gum of this invention can be hardened by use of magnesium sulfate and the presence of magnesium is not a contaminant for aspartate formation. Attempts by Applicant to harden alginic acid hydrogels by dropping beads of the hydrogel into a magnesium sulfate solution were ineffective because the alginic acid hydrogels dissolved in the magnesium sulfate solution.

Solutions of hydrogels of carrageenan, agar, alginic acid and gellan gum were extruded through a 10 ml pipette having an Oxford 810T pipette tip attached to channel the kinetic energy of the hydrogel solutions for dispersing the hydrogel solutions into beads in the calcium or magnesium sulfate solutions. Solutions maintained at elevated temperatures of 1 part of 50% wet weight cells ATCC 11303 and 5 parts of the particular hydrogel were extruded through said pipette arrangement while the temperature of extrusion was allowed to drop to determine the lowest temperature at which each hydrogel/cell mixture could be handled as a solution and extruded to make a gel.

Additionally, the concentration of the respective polymers in the hydrogels were varied to determine the optimum concentration of each polymer which was high enough to make a soft bead in the hardening solution maintained at 5° C. but low enough to be dispersed into beads.

The optimum concentration and extrusion temperature found for each hydrogel is shown in Table 1.

TABLE 1

| HYDROGEL HARDENING SOLUTION | CONC. Gm./L | TEMP. °C. | |
|---|---|---|---|
| CARRAGEENAN | 25 | 60 | 50 Gm./L MgSO$_4$ |
| AGAR | 25 | 37 | 50 Gm./L MgSO$_4$ |
| ALGINIC ACID | 20 | 30 | 5 Gm./L CaCl$_2$ |
| GELLAN GUM | 12 | 41 | 50 Gm./L MgSO$_4$ |

Beads of each hydrogel were produced under the conditions set forth in Table 1. Elevated pressures were required to extrude the very viscous carrageenan and alginic acid hydrogel solutions. The gellan gum and alginic acid beads hardened further as they soaked overnight in the hardening solution. The carrageenan and agar beads did not appear to harden further after overnight soaking.

The hydrogel beads were then cross-linked. First, 5.6 L solutions of 3.3 L water; 51.6 gms. MgSO$_4$; 255.5 gms. disodium phosphate and 58.1 gms. 1,6-hexanediamine were prepared, the pH was adjusted to 7.0 with sulfuric acid and the solution cooled to 5° C. A kilogram of each hydrogel bead recovered from the hardening solutions was added to a prepared solution and mildly agitated for 10 minutes. Then 173 gms. of sodium glutaraldehyde were added and the mild agitation continued for 30 additional minutes. The beads were recovered from the solution and rinsed thoroughly to remove excess glutaraldehyde.

The carrageenan and gellan gum beads were soaked in fumarate solution until the cells contained therewith were dead. The fumarate solution activated the enzymes and broke open the cells. The agar and alginic acid beads dissolved under the reaction conditions and thus are not suitable or operable for this invention.

Activity of beads for ammonium aspartate production is defined as the product of (0.98) (1.64 mol./L) (volume of ammonium fumarate in reactor) (133 qm./mol) (fumarate concentration gm./L) divided by the product of (time required to achieve 98% conversion) (weight of beads in gms.) (190.35).

The gellan gum beads showed an activity of 5.69 while the carrageenan beads had lost most of their activity showing less than 5% of the activity obtained with the gellan gum beads.

Thus, the carrageenan, agar and alginic acid hyrogels are shown as not being capable of producing good quality beads of immobilized aspartase in accordance with this invention. The aspartase is deactivated too quickly when using carrageenan due to the high temperature required to immobilize the cells. The agar dissolves some in the hardening solution and almost completely in the cross-linking solution. The alginic acid requires calcium to harden the beads and then they dissolve during cross-linking.

I claim:

1. A method for immobilization of catalytically-active microbial cells which comprises:
    a) admixing a paste of microorganisms possessing aspartase activity with an aqueous solution of gellan gum containing between 1.0 and 1.8 wt.% gellan gum to produce a mixture containing less than 50 wt.% of the paste of microorganisms;
    b) adding the mixture of part a) drop-wise to an aqueous solution of magnesium cans of sufficient magnesium ion concentration and at a sufficient temperature to harden the gellan gum thereby forming hardened beads containing said microorganisms; and
    c) recovering the hardened beads produced in step b).

2. A method of claim 1 in which the aqueous gellan gum solution has a concentration of gellan gum between 1.2 and 1.8 wt.% and the microorganism paste comprises less than about 50wt.% of the mixture.

3. A method of claim 1 inn which the aqueous gellan gum solution has a concentration of gellan gum between 1.0 and 1.2 wt.% and the microorganism paste comprises less than about 50 wt.% of the mixture.

4. A method of claim 1 in which the microorganism is E. col.

5. A method of claim 1 in which the microorganism is E. coli ATCC 11303.

6. A method of claim 1 in which the concentrations of magnesium ions is between about 0.1 and 0.5 M.

7. A method of claim 1 in which the concentration of magnesium ions is between about 0.1 and 0.4 M.

8. A method of claim 1 in which the gellan gum concentration is between 1.0 and 1.6 wt.%.

9. A method of claim 1 in which the gellan gum has a concentration between 1.2 and 1.6 wt.%.

10. A method for immobilization of catalytically-active microbial cells which comprises:
    a) admixing a paste of microorganisms possessing aspartase activity with an aqueous solution of gellan gum having a concentration of gellan gum between about 1.0 and 1.8 wt.% to produce a mixture comprising less than about 50 wt.% of the paste of microorganisms; and
    b) admixing the mixture of part a) with a porous cationic exchange resin in magnesium ion form said resin being porous enough to permit ingress of microorganisms and having a sufficient magnesium ion charge density to harden the gellan gum.

11. The method of claim 10 wherein said gellan gum concentration is between about 1.2 and 1.8 wt.%.

12. The method of claim 10 wherein said gellan gum concentration is between about 1.2 and 1.6 wt.%.

13. A method of claim 10 in which the microorganism is E. coli.

14. A method of claim 10 in which the microorganism is E. coli ATCC 11303.

* * * * *